(12) United States Patent
Madaras et al.

(10) Patent No.: US 6,565,914 B2
(45) Date of Patent: May 20, 2003

(54) METHOD FOR CONTROLLING DEPOSITED POLYMER ON A SUBSTRATE

(75) Inventors: Jon Michael Madaras, Fairlawn, OH (US); Kenneth Michael Kot, Canton, OH (US); Paul Michael Bujak, Cuyahoga Falls, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 75 days.

(21) Appl. No.: 09/903,042

(22) Filed: Jul. 11, 2001

(65) Prior Publication Data

US 2003/0012867 A1 Jan. 16, 2003

(51) Int. Cl.$^7$ ................................................. B05D 3/12
(52) U.S. Cl. .................. 427/8; 427/9; 427/10; 427/350; 427/434.2
(58) Field of Search ............................ 427/350, 434.2, 427/430.1, 207.1, 8, 9, 10

(56) References Cited

U.S. PATENT DOCUMENTS

| | | | | |
|---|---|---|---|---|
| 3,885,911 A | * | 5/1975 | Habib | 8/115.6 |
| 4,904,928 A | * | 2/1990 | Lewis | 324/636 |
| 4,957,770 A | * | 9/1990 | Howarth | 427/9 |
| 5,826,458 A | | 10/1998 | Little | 73/73 |
| 6,085,437 A | | 7/2000 | Stipp | 34/115 |
| 6,111,651 A | | 8/2000 | Shakespeare | 356/429 |
| 6,163,733 A | | 12/2000 | Rubel | 700/130 |

OTHER PUBLICATIONS

US 6,134,809, 10/2000, Stipp (withdrawn)

"Design Aspects of Stripline Resonator Sensors for Industrial Applications" by M. Fischer, P. Vainikainen and E. Nyfors, published as Helsinki University of Technology, Espoo (Finland), Radio Lab Report No. S–214 (no date).

"Measurement Electronics of Industrial Microwave Resonator Sensors", Report S 194 (Nov. 1991), a PhD. Thesis by P. Vainikainen, Helsinki Univ. Of Technology, Espoo, Finland.

Performance Analysis of Measurement Methods of Industrial Microwave Resonator Sensors by P. Vainikainen, Helsinki Univ. of Technology, Espoo, (Finland), Report S 193, Radio Lab. 1 (no date).

Profile Inversion of Stratified Dielectric Media Using the Two–Step Reconstruction, by V. A. Mikhnev and P. Vainikainen, Institute of Applied Phys. Minsk, Byelorussia, Conference paper (PA). (no date).

"Reconstruction of the Permitivity Profile Using a Nonlinear Guide Wave Technique" by V. A. Mikhnev, E. Nyfors and P. Vainikainen, Helsinki Univ. of Technology, Espoo, Finland (no date).

"Measurement of Dielectrics at 100 GHz with an Open Resonator Connected in a Network Analyzer" by T. M. Hirvonen, P. Vainikainen, A. Lozowski and A. V. Räisänen, Radio Lab, Helsinki Univ. of Technology, Espoo, Finland (no date).

* cited by examiner

Primary Examiner—Katherine A. Bareford
(74) Attorney, Agent, or Firm—David E. Wheeler; Nancy T. Krawczyk

(57) ABSTRACT

A resonant cavity frequency sensing device is used to sense the moisture content of a substrate. Data obtained by the sensing device can be used in a feedback loop in the apparatus employing the device, to help control the operation of the apparatus in order to obtain consistent results. The sensor may employ one pair of sensing plates or an array of pairs of sensing plates to obtain data from each part of the substrate. In an illustrated embodiment, the device is used to monitor and control dip uptake in a fabric adhesive dipping process.

6 Claims, 17 Drawing Sheets

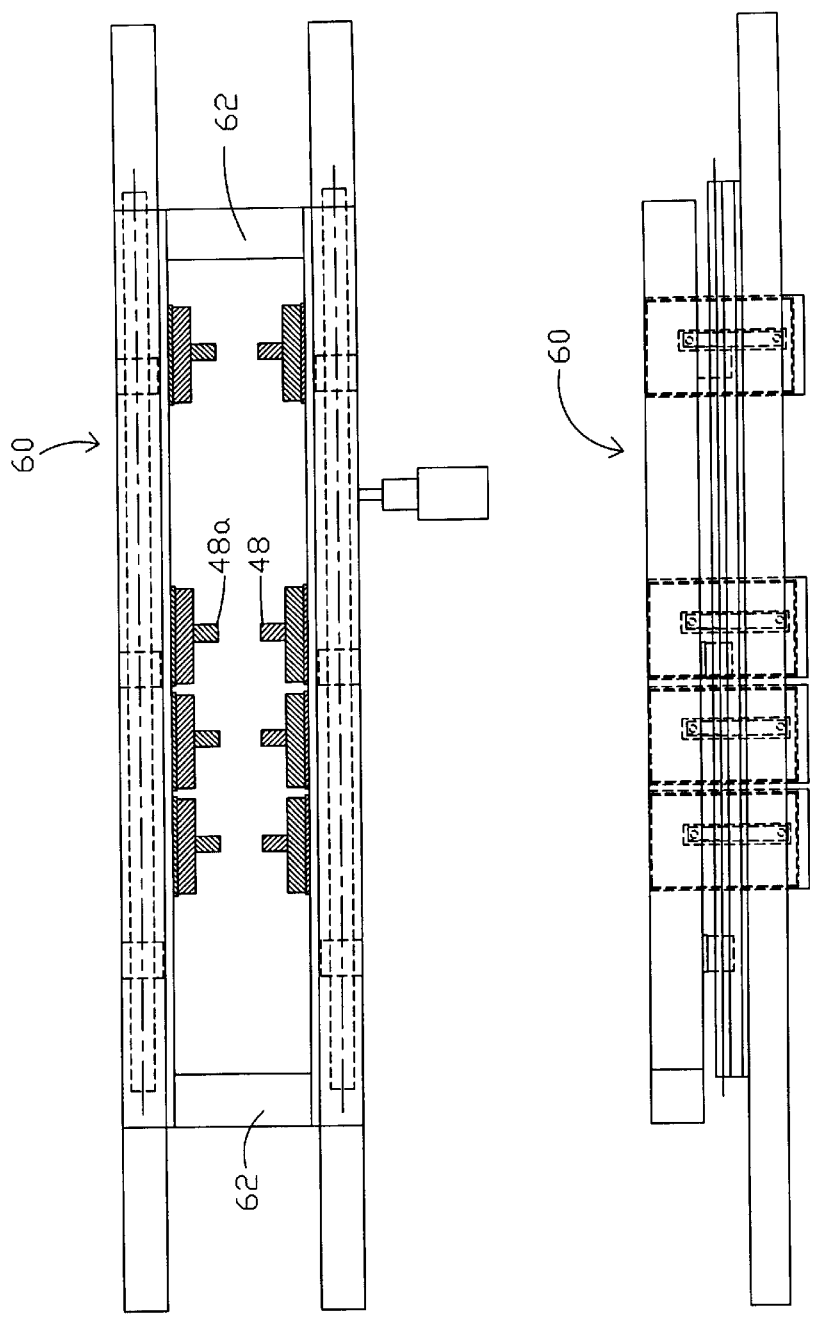

METHOD FOR CONTROLLING DEPOSITED POLYMER ON A SUBSTRATE

FIELD OF THE INVENTION

The invention relates to a method and apparatus for measuring and controlling the application of elastomers and adhesives to a substrate.

BACKGROUND OF THE INVENTION

In the manufacturing of products wherein a liquid rubber or an adhesive is applied to a substrate, such as in the tire industry, wherein an adhesive is applied to fabric reinforcement to form a reinforced component for a tire, such as a carcass ply, belt, or chafer, the liquid rubber or adhesive is often applied to the substrate in a dipping process. In the prior art, using tire manufacturing for illustrative purposes, a fabric is continuously passed through a fabric dip unit that contains one or more trays containing the liquid rubber or adhesive, such as is illustrated in U.S. Pat. No. 5,407,701, issued Apr. 18, 1995, said patent being incorporated herein by reference. The dip unit may have associated therewith, as is illustrated in FIG. 2 herein, vacuum units that are adapted to remove excess liquid rubber or adhesive from the fabric and prepare the fabric for entry into a drying oven.

Quality control of the dipping operation is provided by manual inspection supplemented by physical tests that are designed to determine the amount of adhesive or liquid rubber that has been picked up in the dipping process. One test compares the weight difference of the fabric roll before and after the fabric has undergone processing in the fabric dip unit. Another test chemically dissolves the fabric to determine the amount of adhesive. The prior art inspection methods are labor intensive, not real-time, time consuming and expensive.

For more than thirty years there have been attempts to automate the inspection of a dipped substrate. One such attempt employed a microwave sensor. Although the apparatus apparently worked for its intended purpose, a microwave sensor needs to be close to the substrate it is sensing, and the first such attempt was damaged by the first splice it encountered.

Rubel in U.S. Pat. No. 6,163,733, issued Dec. 19, 2000, describes a monitor and malfunction detector for the thread feed of a textile machine. The monitor combines electronic information and mathematical analysis of the movement of the thread, including speed, tension, and fiber consistency, thereby permitting the determination of: (1) the presence of knots and inconsistencies in the thread; (2) the operating status of the textile equipment and thread feed; (3) the prediction of problems based on the change of operating characteristics, including speed, tension, draw and duty cycle patterns; (4) the control of the textile machine being monitored; (5) the diagnosis of mechanical faults; (6) production accounting; and (7) needle burr detection.

The monitor also employs a signal comparison incorporating differential circuitry, pattern recognition, and averaging functions to achieve these goals.

Shakespeare, in U.S. Pat. No. 6,111,651, issued Aug. 29, 2000, describes an apparatus for measuring properties of a moving web. The apparatus provides a stimulus, which is directed onto the moving web by an excitation element, and the effect of the web on the stimulus is measured with a detection element. At the measuring point, the web is supported by a measurement support sheet. The measurement support sheet comprises at least two regions having different but known-responsiveness to one or more forms of stimulus, or causing different but known transformation to one or more forms of stimulus.

Stipp, in U.S. Pat. No. 6,085,437, issued Jul. 11, 2000, describes a process and apparatus for removing water from a fibrous web. In the process, the fibrous web having a moisture content of from 10% to about 90% is impinged by an oscillatory flow-reversing gas having a frequency of from 15 Hz to 1500 Hz. The apparatus includes a gas-distributing system comprising a plurality of discharge outlets designed to emit the oscillatory flow-reversing impingement gas onto the web. The impingement gas is used to remove the moisture from the web. The apparatus includes a web support designed to receive a fibrous web and to carry it in the machine direction, at least one pulse generator designed to produce oscillatory flow-reversing air or gas, and at least one gas-distributing system in fluid communication with the pulse generator.

Little, in U.S. Pat. No. 5,826,458, issued Oct. 27, 1998, describes a moisture-detection meter having a sensing head, which has a single chamber with an open top. A dielectric resonator member is provided in the chamber. The sensing head includes a field generator used to generate an oscillating electric field in the chamber. The resonator member and the field interact to produce at least one field component, which is directed out of the open top of the chamber to interact with stock passing over the sensing head. A detection device is provided to detect the frequency of resonance of the field compact after interaction with the stock, and an indicator device is provided to give an output indicative of the moisture content of the stock.

Stipp, in U.S. Pat. No. 6,134,809, issued Oct. 24, 2000, describes a process and apparatus for removing water from a fibrous web. This patent is apparently related to the earlier described Stipp patent since the description is basically the same.

Also of interest as background information for resonators used in industrial applications are "Design Aspects of Stripline Resonator Sensors for Industrial Applications" by M. Fischer, P. Vainikainen and E. Nyfors. published as Helsinki University of Technology, Espoo (Finland), Radio Lab. Report No. S-214; "Measurement Electronics of Industrial Microwave Resonator Sensors", (November 1991), a Ph.D. Thesis by P. V. Vainikainen; Helsinki Univ. of Technology, Espoo, Finland; "Performance Analysis of Measurement Methods of Industrial Microwave Resonator Sensors", by P. Vainikainen, Helsinki University of Technology, Espoo, Finland, Radio Lab. 1; 1999 Institution of Electrical Engineers, all reports; "Profile Inversion of Stratified Dielectric Media using the Two-Step Reconstruction, by V. A. Mikhney and P. Vainikainen, Institute of Applied Phys., Minsk, Byelorussia; Conference paper (PA) "Reconstruction of the Permittivity Profile using a Nonlinear Guided Wave Technique" by V. A. Mikhnev, E. Nyfors and P. Vainkainen, Helsinki Univ. of Technology, Espoo, Finland; "Measurement of Dielectrics at 100 GHz with an Open Resonator Connected in a Network Analyzer" by T. M. Hirvonen, P. Vainikainen, A. Lozowski and A. V. Raisanen, Radio Lab., Helsinki Univ. of Technology, Espoo, Finland.

SUMMARY OF THE INVENTION

A method for applying a polymer to a substrate comprises the steps of (a) providing means for depositing a polymer on a substrate; (b) applying polymer to a substrate; (c) providing sensor means for detecting the amount of polymer which has been applied; (d) sensing the amount of polymer that has been applied; (e) providing vacuum means for removing excess polymer from the substrate after the polymer has been applied, and (f) removing excess polymer from said substrate.

In the illustrated embodiment, the method comprises the further steps of: (g) using a dipping operation to apply the polymer in step (b), and (h) using a resonant sensor to detect the amount of polymer applied in step (d). In the method information from the sensor in step (d) is used to control the vacuum used to remove excess polymer in step (f). Information from the sensor is combined with information from fabric specifications, line speed, adhesive formula and solids level to control polymer application and the vacuum used to remove the excess polymer.

In the illustrated embodiment, a base line resonant frequency for a specific substrate is established; a second resonant base line for the substrate coated with a desired amount of polymer is established; and the vacuum in the vacuum means is controlled using the resonant frequency data such that when the content of polymer on the substrate is too high the vacuum is increased, and when the content of the polymer is too low the vacuum is decreased.

The method may be used with tenter frames, calenders, conveyors, or any similar equipment which is used to transport a substrate.

Also provided is an apparatus for applying a polymer to a substrate comprising (a) directing and handling means for directing and handling a substrate material; (b) application means associated with the directing and handling means for applying a polymer to the substrate; (c) sensing means associated with the directing and handling means located on the directing and handling means in a location proximal to the substrate and down stream of the application means; and (d) data collection means in communication with the sensing means for accepting and collating data from the sensing means.

The apparatus may further comprise processing means associated with the data collection means and the directing and handling means for using the data from the sensing means to set operational parameters for the directing and handling means. The apparatus may comprise any conveying apparatus as described above, and sensing means comprising a resonant frequency sensor. The application means may comprise a dip through which the substrate passes. Data collection means may comprise an analyzer and the processing means may comprise a computer. The apparatus may further comprise vacuum means for removing excess dip from the substrate after application of the dip to the substrate.

When the data processing means is a computer, the computer may be programmed to control at least one of the vacuum in the vacuum means, the rate of the substrate through the equipment, the temperature of ovens associated with the equipment, and the width and other parameters of the directional handling means.

The resonant frequency sensor comprises a frequency activator and at least a pair of opposed resonator plates. A first array of resonator plates may be opposite a second array of resonator plates on each side of the substrate.

The resonator plates may be hourglass shaped. Arrays of hourglass shaped resonator plates may have a width corresponding to the width of the substrate.

It is a continuing goal in the art to reduce the expense and improve the quality of substrate processing, especially where a liquid rubber or adhesive is applied to a substrate.

Other objects of the invention will be apparent from the following description and claims.

BRIEF DESCRIPTION OF THE DRAWINGS

The invention will be described by way of example and with reference to the accompanying drawings in which:

FIG. 11 illustrates a plan view of an alternative embodiment of a resonant cavity sensor of the invention.

FIG. 12 illustrates a side view of the apparatus of FIG. 11.

DETAILED DESCRIPTION OF THE INVENTION

For ease of illustration, the present invention will be described as it relates to processing rolls of fabric on a fabric dip unit designed to manufacture carcass plies, belts, and other fabric reinforcements for pneumatic tires, conveyor belts, or other products. Those skilled in the art will recognize that the apparatus and methods described herein can be used for manufacturing similar products wherein a substrate is dipped with a liquid rubber or adhesive in a manufacturing process, and that the invention can be used in other methods. For example, spray methods or calendering methods may be used to apply a material in liquid form to a substrate.

Figure 2:
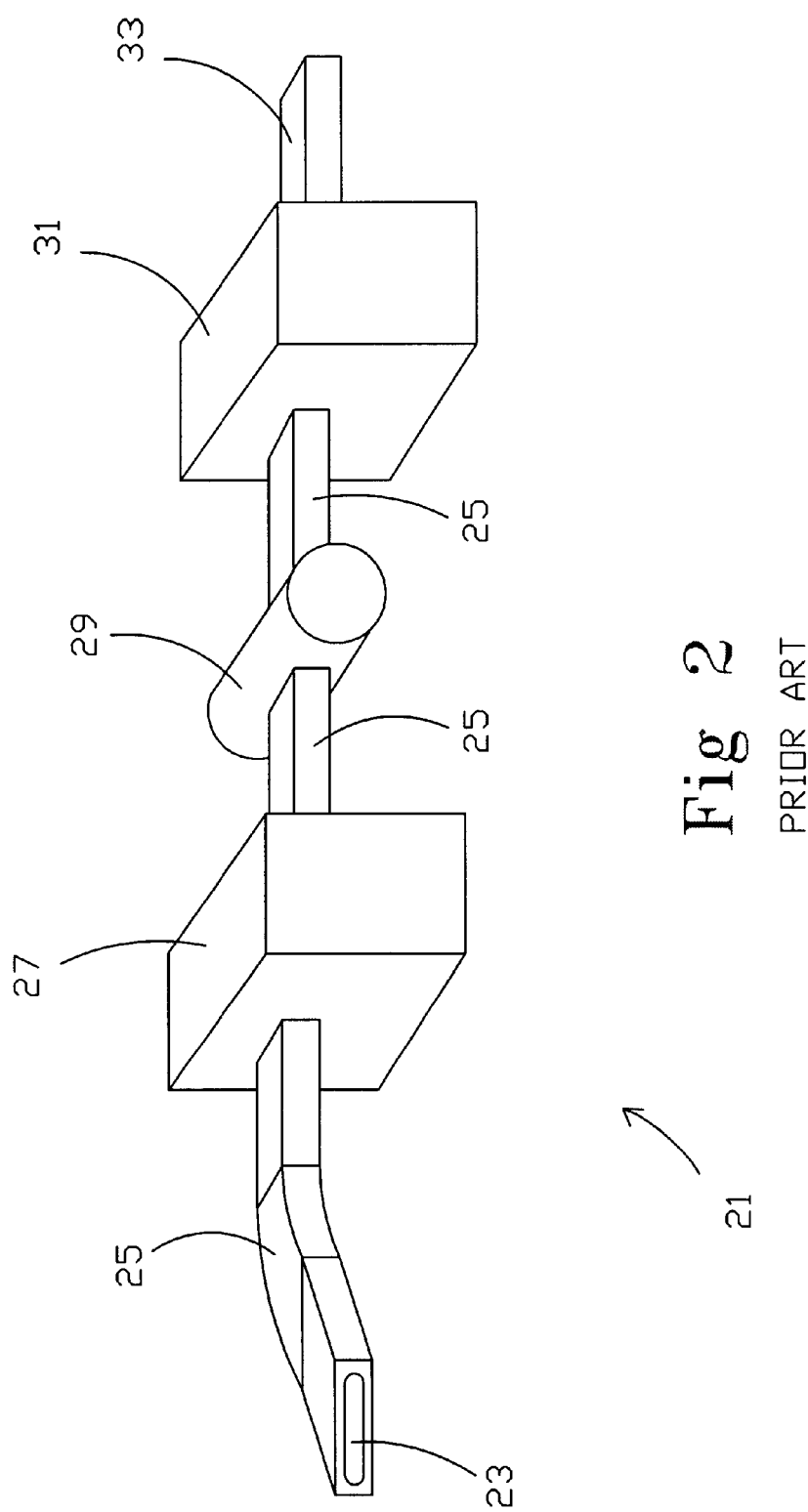
FIG. 2 illustrates a prior art vacuum system used for removing excess dip from a substrate.

The substrate used in the manufacturing process may comprise any suitable material, and in the illustrated embodiment may be selected from the group comprising nylon, polyester, rayon, fiberglass, aramid, and carbon fiber. In the fabric dip unit, a fabric web passes through (or is dipped into) one or more adhesive solution baths, and passes through a series of ovens where the adhesive is dried and the fabric is heat-treated to obtain the desired physical properties. The adhesive application is performed by submerging the fabric web into a bath of the adhesive solution and removing the excessive amounts by using a vacuum system as illustrated in FIG. 2. By adjusting the level of vacuum, the amount of adhesive, usually measured in percent additional weight added to the weight of the original roll of fabric, can be controlled. The adhesive solution usually comprises about 80% water and about 20% solids, and the water is evaporated from the fabric in the ovens so that only the solids remain.

For ease of illustration, only one vacuum unit is shown in FIG. 2. In the testing done by applicant, one such unit was deployed on each side of the fabric as it passed through the dipping unit.

Figure 1:
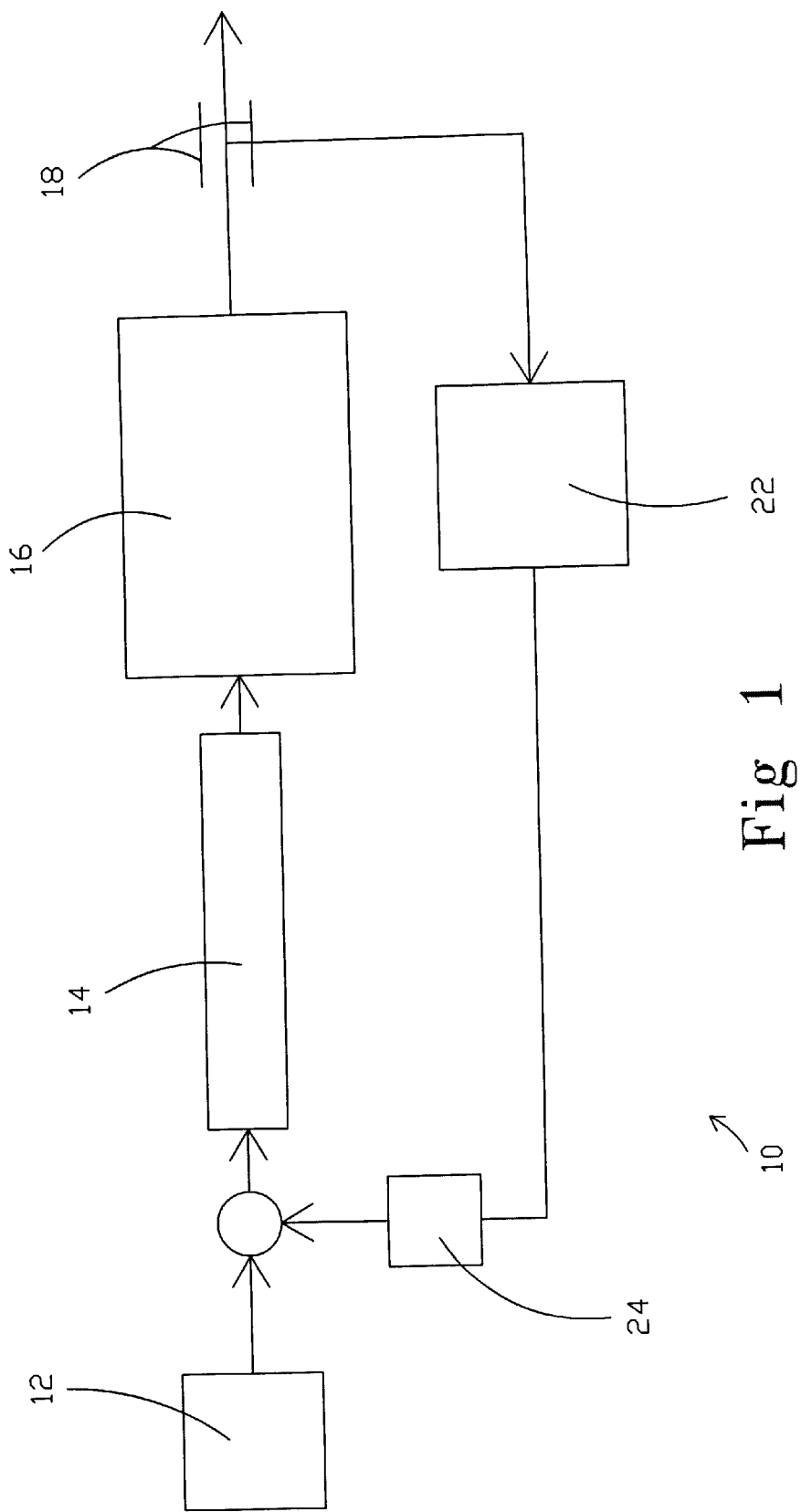
FIG. 1 illustrates a schematic block drawing of the apparatus of the invention used to control a dipping operation.

With reference now to FIG. 1, a block diagram 10 illustrates the control system used in the apparatus of the invention. A target value 12 is established which optimizes the amount of vacuum needed to remove excessive amounts of adhesive from the fabric while leaving optimal amounts of adhesive adhered to the fabric. This target value for adhesive may vary depending on the type of adhesive used and can be obtained for a specific combination of fabric and adhesive by routine experimentation. In the operation of the control system, the target value 12 is compared with the analyzed value 24 as determined by sensor system 18 and network analyzer 22, and the differences are used by computer control unit 14 to control the amount of vacuum 16 applied at the dipping unit. The process is shown in a loop, illustrating the fact that analysis is continuous and values obtained are continuously compared to the target value, so that the vacuum can be controlled on a continuous basis to obtain a substantially uniform result.

With reference now to FIG. 2, the vacuum system used is a dewebber system 21, which is conventionally used, in the prior art. The dewebber 21 comprises a head 23, which is located proximal to the fabric as it exits the adhesive solution or dip bath. Any excess adhesive pulled from the fabric by head 23 passes through ducts 25 and is deposited in collector box 27. The vacuum is created by fan 29, which is connected by the ducts 25 to collector box 27, and the other components of the system. Filter 31 is provided to trap any particulate matter that may be caught in the vacuum stream to prevent its release into the environment through exhaust 33.

Figure 3:
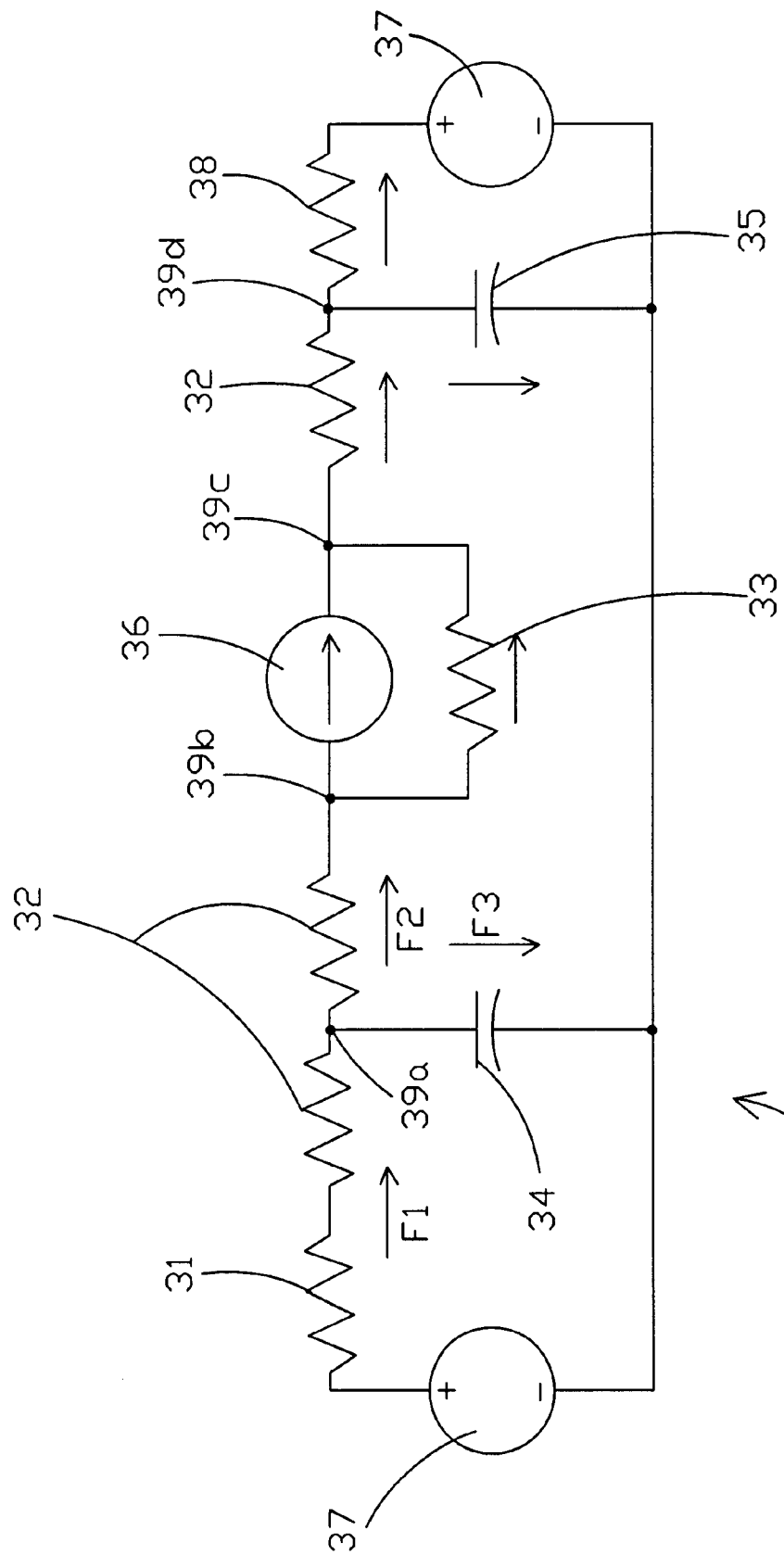
FIG. 3 illustrates an electrical type diagram modeling the control system of the apparatus.
Figure 4:
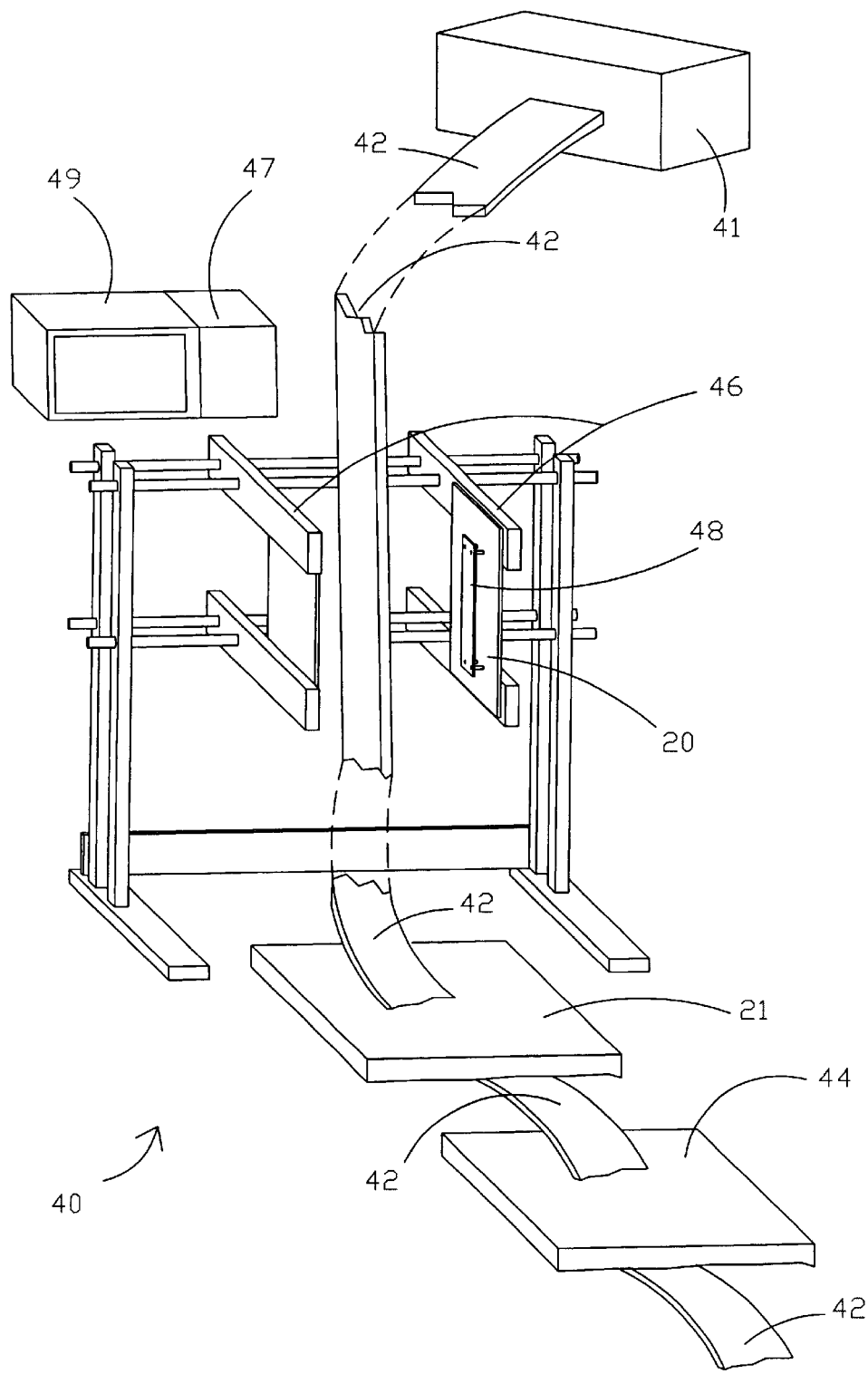
FIG. 4 illustrates an end view of an exemplary apparatus of the invention.

With reference now to FIG. 3, electrical engineers often use symbols relating to resistors, capacitors, and inductors as analogs to mechanical parts when modeling mechanical systems. FIG. 3 is an electrical type diagram illustrating the control process as it relates to the vacuum system. In the electrical type layout 30, the number 37 represents the atmospheric pressure present at the dewebber head in the proximity of the processed fabric and at the exhaust 33, respectively. Resistance 31 corresponds to the dewebber orifice (at head 23) and the number 32 correspond to the ducts in the vacuum system. 39a corresponds to the pressure in the collector box, 39b corresponds to the pressure seen in the fan chamber at its entrance point, and 39c corresponds to the pressure in the fan chamber at its exit point. 39d corresponds to the pressure in the filter box. The fan in the diagram is represented by the number 36. Resistance 33 represents the fan losses, i.e., the difference seen between the pressure at point 39b and the pressure at point 39c. Capacitor 34 represents the collector box and capacitor 35 represents the filter box. The flows in each portion of the apparatus may be monitored to make sure that they stay in balance, and when the flows go out of balance, head angles, tension on the web, and dampers and lips and filters may be adjusted. The apparatus is controlled primarily by the readings provided by sensor system 18, however, wherein if sensor system 18 indicates that there is too much adhesive on the fabric, fan speed will be increased, and if there is not enough adhesive on the fabric, fan speed will be decreased.

The system may be enhanced by providing for recirculation of the dip, to ensure consistency of the dip.

With reference now to FIGS. 4 to 7, in the illustrated embodiment, prototype apparatus 40 comprises a frame structure 46 which is placed downstream of dip bath 44 and vacuum 21 (each shown as black boxes) and has mounted thereon sensor plates 48. Data from sensor plates 48 is fed into analyzer 47 and computer 49 to control the processing described above for controlling the vacuum in dewebber 21. Sensor plates 48 are mounted on much larger grounding or shielding plates 20, which are provided to eliminate disturbance of the electric field by movement of personnel and to eliminate the effects of ambient conditions in the area of the sensors. After passing between sensor plates 48 in this portion of the process, fabric 42 is directed into ovens 41 (shown as a black box).

Sensor plates 48 comprise a portion of a high-frequency resonant cavity measurement device similar to those used in the paper industry to monitor paper. In the illustrated embodiment, the two parallel plates, which are the resonator or sensor plates, are located on each side of the fabric web as it exits the adhesive dip bath and dewebber heads. By generating a high frequency field between the parallel plates, the resonant frequency for the empty space between the plates is determined. In the illustrated embodiment, the 350 megahertz level was used because it produced the optimal frequency for lowest cost hardware selection. Other frequencies can be used to optimize each application. The frequency changes or shifts when something passes between the plates, and it has been found according to the present invention that the amount of shift can also be correlated to the amount of dip (liquid rubber or adhesive solution) that has been retained on the fabric. Using this correlation, the amount of adhesive applied to the fabric can be measured and controlled during the application process so that all areas of the fabric can be monitored as it is dipped, reducing the need for human inspection. Accurately controlling the adhesive application on the fabric may provide a more uniform dip and better control of adhesive consumption.

The analyzer used in the prototype was a Hewlett Packard 8752C network analyzer. The network analyzer is used to measure the frequency response properties of the sensor. Information such as resonant frequency and the Q factor are computed. The quality factor Q of the resonator is defined as the ratio between the stored energy in the resonator and the dissipated power per unit time $$Q = \frac{\omega_o W_o}{P_d}$$

where $\omega_o$ is the resonator frequency, $W_o$ is the stored energy, and $P_d$ is the dissipated power. The Q factor is well known to those skilled in this art.

The network analyzer uses a GPIB interface to communicate with a personal computer having a GPIB interface card. The GPIB (general purpose interface bus) was specifically designed to connect computers, peripherals and laboratory instruments so that data and control information can be exchanged between them. It is also known as IEEE-488 or HPIB, and is electrically equivalent to IEC-625 bus. It is defined in the IEEE standard 488.1-1987 Standard Digital Interface for Programmable Instrumentation.

In simple terms, the cavity resonator comprises two parallel conductors. The conductors are excited by the network analyzer (frequency sweep) and the resonant frequency corresponds to the greatest reflection coefficient. The resonant frequency will change depending on the amount of water between the plates and the kind of material, which is interposed between the plates. Although there are small frequency shifts caused by the presence of a fabric between the sensor plates, moisture accounts for about (at least) a thirty-fold increase in the shift. The apparatus, accordingly, measures primarily the moisture content of a substrate.

Figure 5:
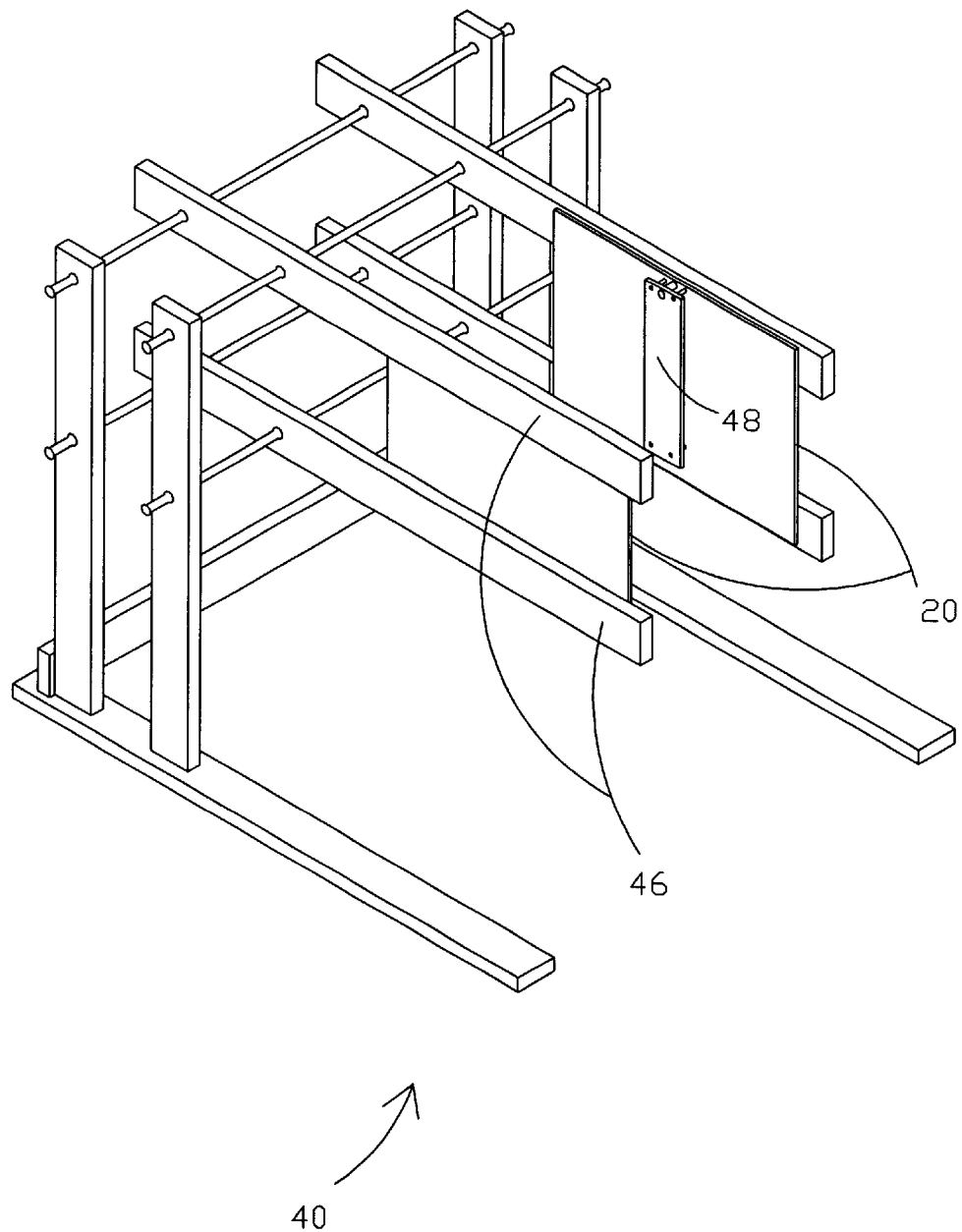
FIG. 5 illustrates an enlarged perspective view of the sensing portion of the apparatus.
Figure 6:
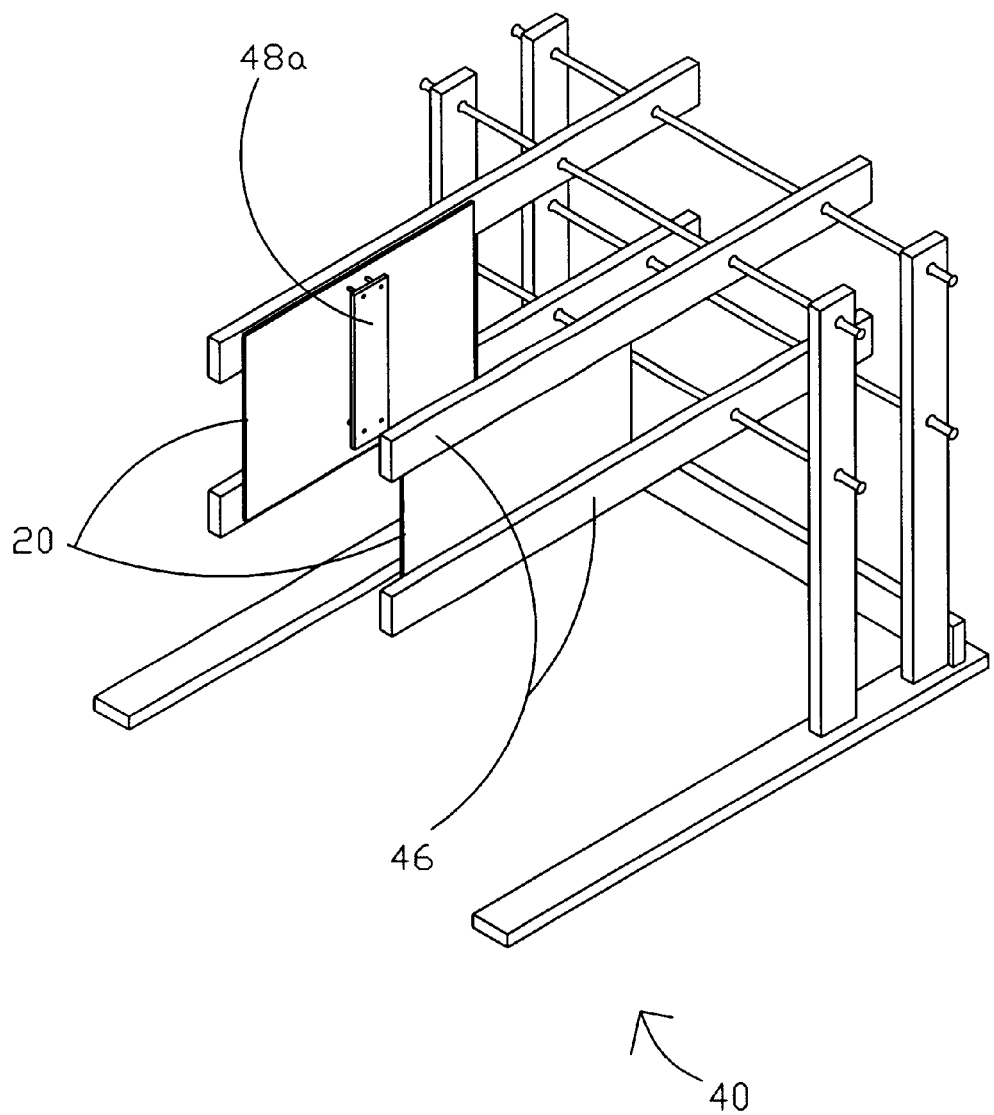
FIG. 6 illustrates an enlarged perspective view of the sensing portion of the apparatus, from the opposite perspective from FIG. 5.
Figure 7:
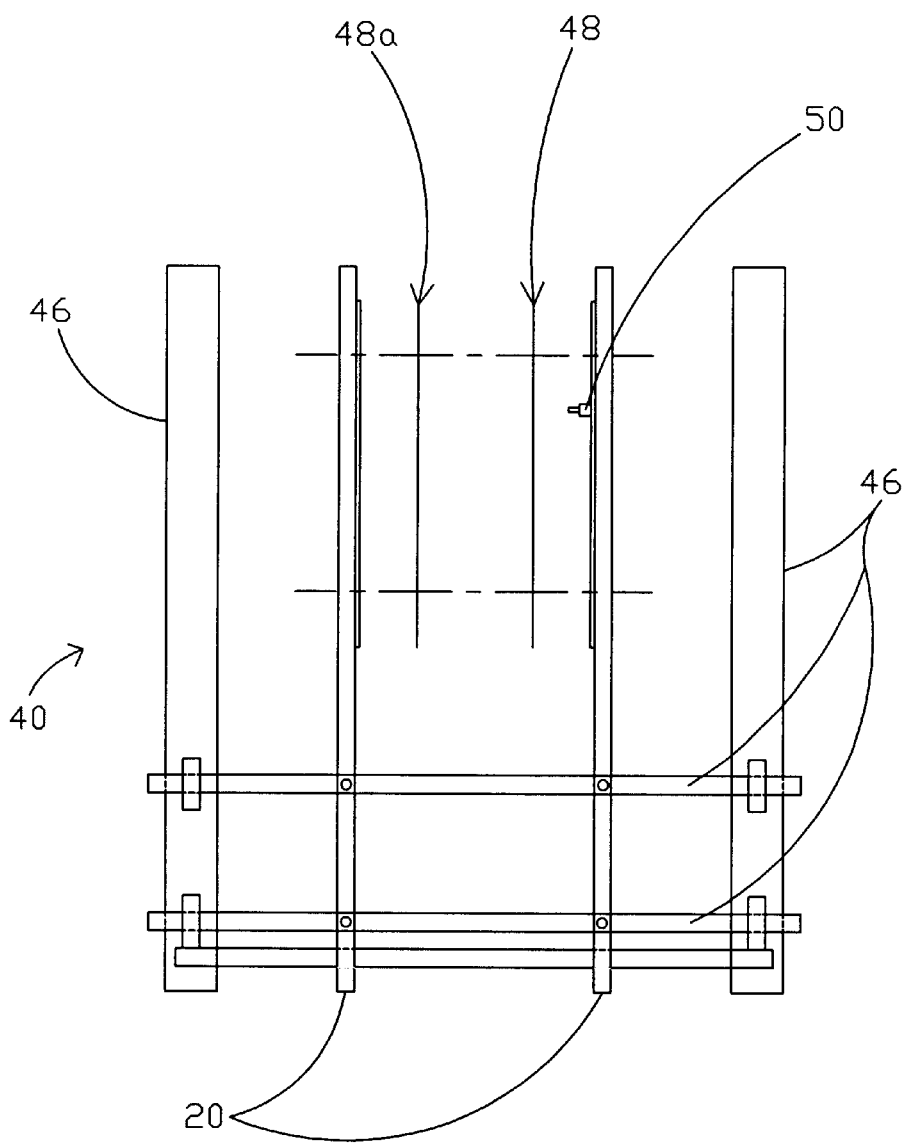
FIG. 7 illustrates an end view of the apparatus.

FIGS. 5–7 illustrates enlarged perspective views and an end view of the prototype sensing unit of the invention. The frame 46, shielding (grounding) plates 20 and sensor plates 48 have been described with reference to FIG. 4. In the operation of the sensor, activator 50 (FIG. 7) is used to create a high frequency sweep of the system. The frequency initiated in activator 50 settles into a resonant frequency response in the sensor plate 48. The resonant frequency of sensor plate 48, in turn, creates a further resonant response in sensor plate 48a (FIG. 6) which is mounted on the opposed grounding plate 20. In actuality, an electromagnetic field is established between the two resonator plates. The frequency generated by activator 50 is known, and the frequency of the resonant response set up between sensor plates 48 and 48a can be measured.

If an object is interposed into this electric field between sensor plates 48 and 48a (such as wet fabric 42) this causes a frequency shift which can also be measured. It has been found, in accordance with this invention, that the frequency shift is stable. Stable enough, in fact, that minor alterations of the object can cause a further frequency shift that can also be measured, and can be quantified such that the amount of shift can be correlated with the amount of moisture present.

Figure 8:
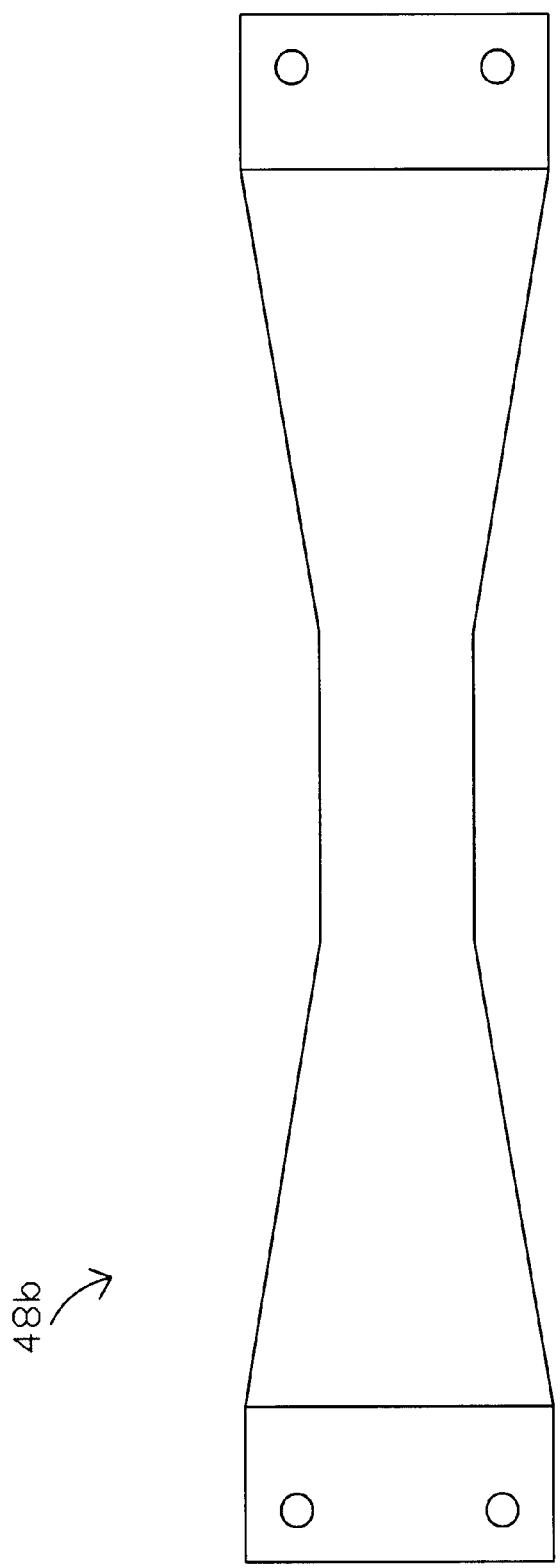
FIG. 8 illustrates an embodiment of a sensing plate of the invention.

With reference now to FIG. 8, in the initial evaluation of the prototype of the invention, one of the objects of the evaluation was to determine if the shape of the sensor plate produced a different response. Rectangular sensor plates (48, 48a) were compared with hour-glass shaped sensor plates (48b), such as shown in FIG. 8, and it was determined that hour-glass shaped sensor plates (48b) had a different resonant frequency than the rectangular shaped plates (48, 48a). Although it is believed that further optimization of the sensor plate shape can be made, for the experiments herein the rectangular shaped sensor plate is preferred. For other uses, different shaped sensor plates can be used.

Figure 9:
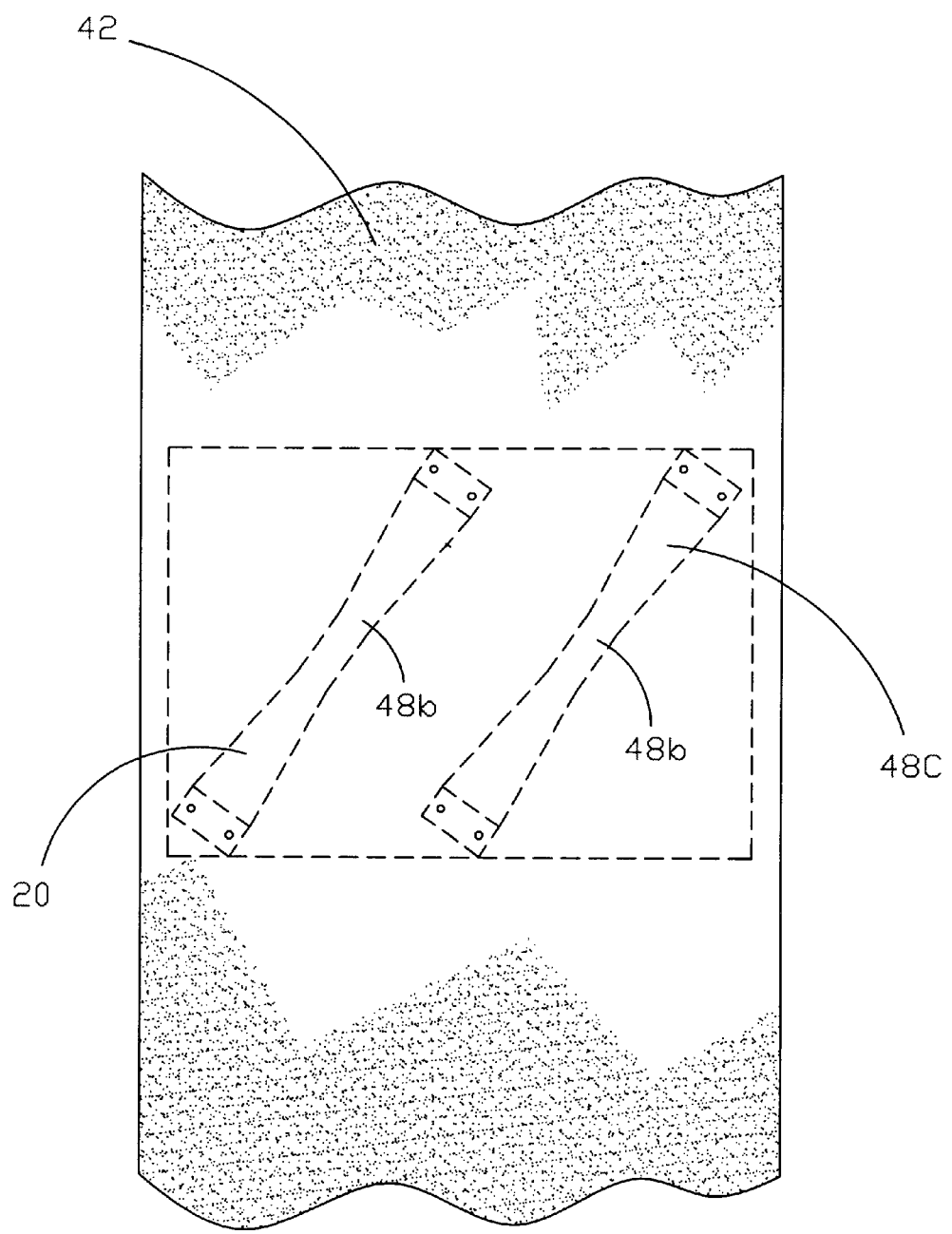
FIG. 9 illustrates an array of sensor plates, which may be used in the apparatus of the invention.
Figure 10:
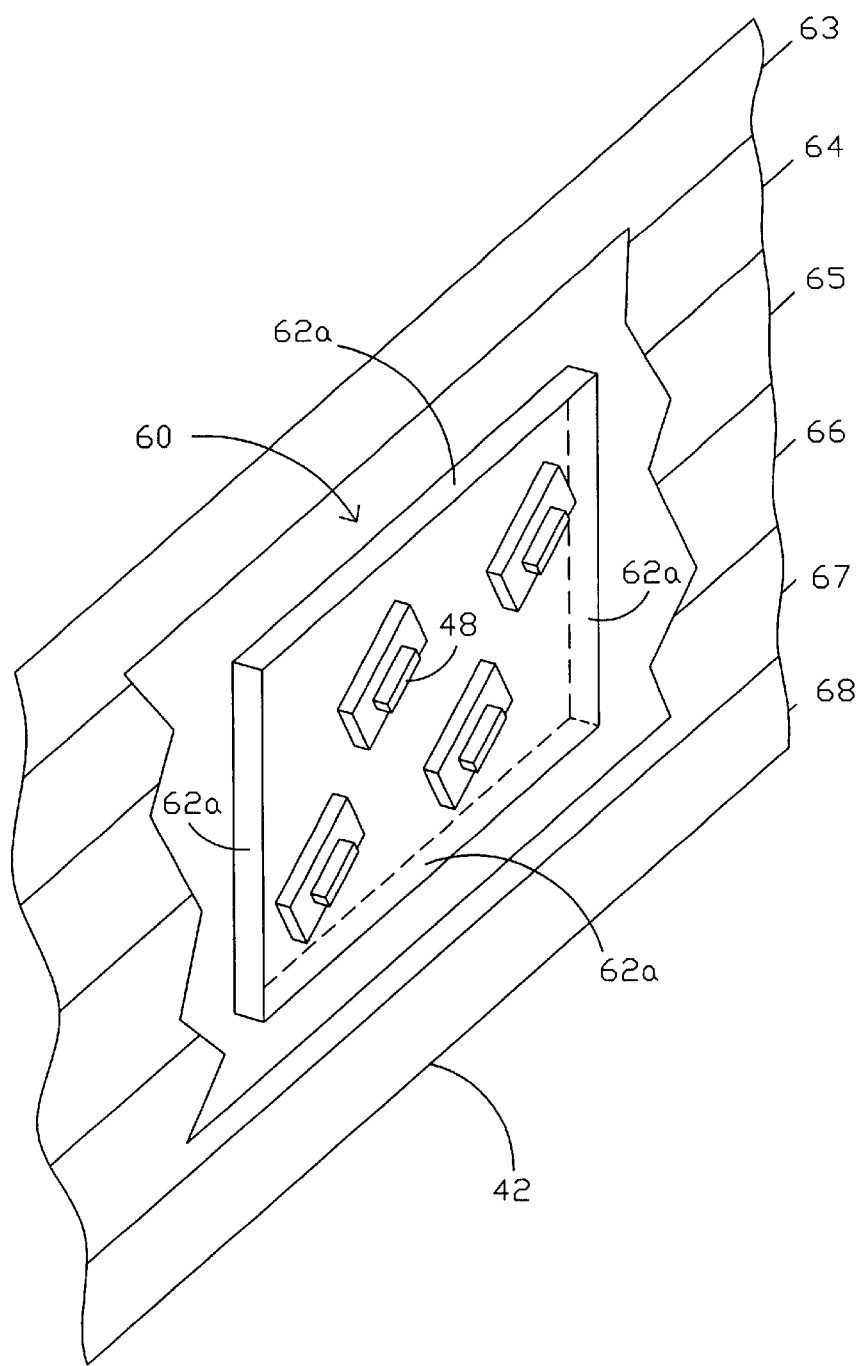
FIG. 10 illustrates a perspective view of an alternative embodiment of an array of sensor plates of the invention.
Figures 13, 14:
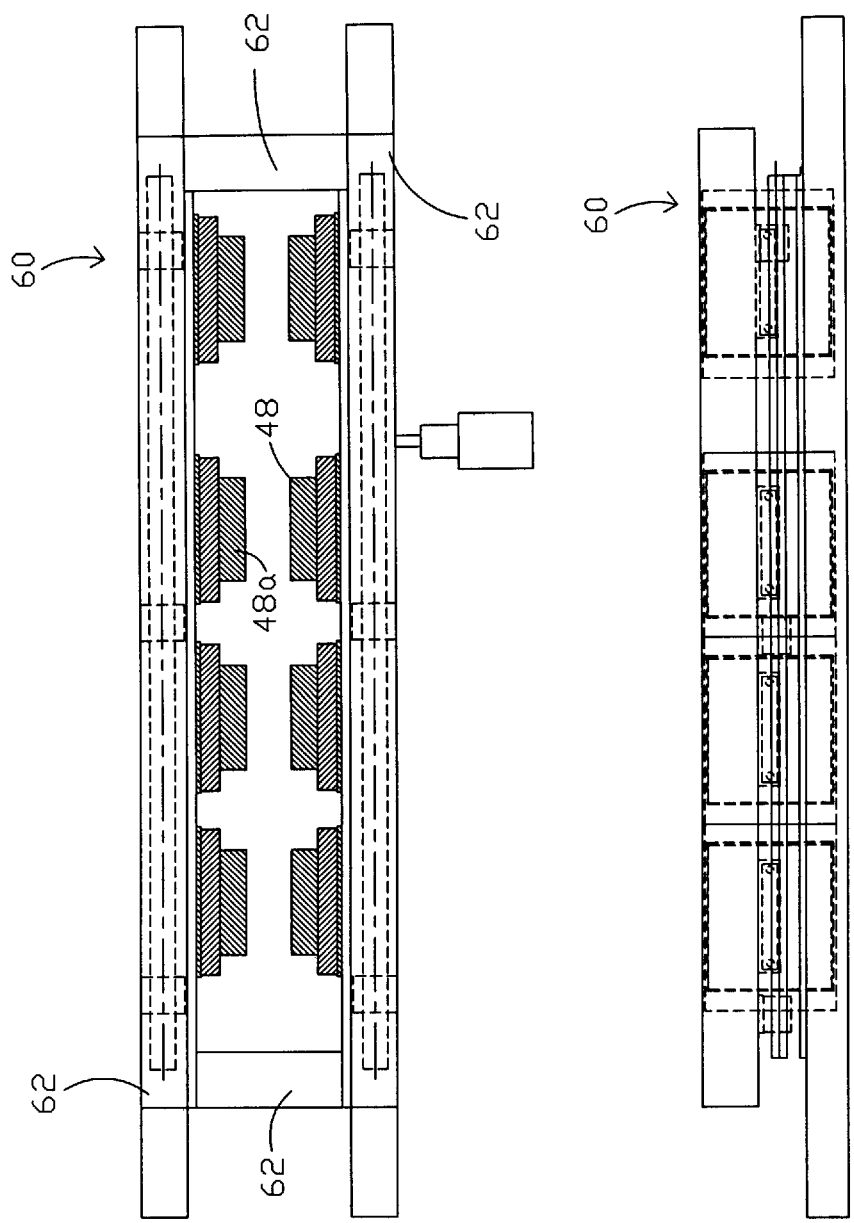
FIG. 13 illustrates a plan view of a third embodiment of the invention.
FIG. 14 illustrates a side view of the apparatus of FIG. 13.

With reference now to FIG. 9, although a pair of single sensor plates (48, 48a) was used to prove the concept of the present invention, the initial testing has shown that there is a benefit to providing sensor plates to cover the full width of the fabric. It is contemplated this full coverage can be provided by using an array 48C of sensor plates. Although the sensor plates can be used from 0° to 90°, in FIG. 9, the sensor plates (48b) are shown disposed on a 30° to 60° angle, preferably a 45° angle to maximize fabric coverage, while minimizing the number of sensor plates needed.

With reference now to FIGS. 10, 11, 12, 13 and 14, in alternative embodiments, sensor plates 48 may be disposed in rigid O-frame 60 which is designed to be movable relative to the apparatus on which the substrate is treated. The O-frame has rigid sides 62, which shield the sensors from outside influences and help protect the sensors from physical damage from the passing substrate. The sensor plates may be further shielded from outside influences by having raised sides 62a on the O-frame. The sensors are adequately spaced so that the electromagnetic fields associated with the sensors do not interfere with one another.

In its operation, the O-frame can be moved from side to side in the treatment apparatus, so that on one stroke of O-frame 60, fields 64, 66 and 68 of the fabric are monitored, and on a second stroke, fields 63, 65 and 67 of the fabric are monitored. Although not every portion of the fabric will be monitored using this procedure, each field of the fabric will be covered sufficiently that suitable balance of the dipping apparatus can be maintained.

In the illustrated embodiment, it is anticipated that the O-frame will remain stationary between strokes. In other embodiments it may be desirable to keep the O frame in constant motion.

In the embodiment illustrated in FIGS. 11 and 12 the sensors are oriented vertically (at 0° with respect to the direction of movement of the fabric). Such an orientation provides great sensitivity since the length of the plate is disposed over a narrow field. In the embodiment illustrated in FIGS. 13 and 14 the sensors are oriented horizontally (at 90° with respect to the direction of movement of the fabric). Such an orientation provides coverage of a wider field, although the sensitivity may be diminished as compared to that seen in the embodiment of FIGS. 11 and 12. The sensor plate may be disposed at any angle between 0° and 90° as may be required (see FIG. 10) for optimization of a particular process.

In the illustrated embodiment, the O-frame comprises a 20-inch (50.8 cm) by 120 inch (304.8 cm) box which is moved in a 12 inch (30.5 cm) stroke. The sensor plates are separated by a distance of 12 cm (centimeters).

As discussed above, the spacing between the plates must be accurately maintained to provide meaningful data, and the O-frame is sufficiently rigid to maintain such spacing.

The control system for the apparatus has been analyzed and modeled based on the parameters illustrated in FIGS. 1 and 3. This model is used to design the controls for the apparatus.

In summary, the sensor system has two identically sized metallic resonator plates (a.k.a. sensors or sensor plates) separated from, but parallel to, each other. The resonator plates are not connected to ground. The electronic equipment sweeps or excites a variable high frequency (0.1 GHz to 1 GHz) onto one of the resonator plates until a resonant frequency is established. An electromagnetic field is generated in the empty space between the two plates. There will be no change to the resonant frequency induced when most dry substrates, such as woven fabric, are introduced. When a wet substrate of some notable dielectric constant, however, such as adhesive coated fabric, is introduced into this space, the field will react and cause a resonant frequency shift or change. The amount of frequency shift can be correlated to the amount of liquid adhesive applied to the fabric, which, in turn, can be controlled by adjusting the adhesive application device. Changing the geometry of the resonator plates, the gap between the parallel plates, or other changes can modify the resonant frequency level and strength of the field. The amount of shift of frequency varies with the amount of adhesive being applied, which is controlled by a closed loop control system that connects the resonant cavity apparatus, the frequency generator/reader, and the adhesive application device.

It is further contemplated that additional modifications may be made to the sensor setup of the invention. For example:

(1) a control sensor, which measures the base frequency, may be placed outside of the area of the fabric web.
(2) For a multi-sensor application, having one frequency generator with switching electronics to scan each sensor's field optimizes the control system. This system can also connect several adhesive applications stations.
(3) The control system can be designed as a quality indicator to alarm or stop the process if non-uniformities, such as streaks of heavy dip or low dip pick-up, are sensed.
(4) The control system can also be designed to optimize the application and/or vacuum removal of the adhesive by determining the influence of factors such as tension level and variation of vacuum uniformity.

The operation of the apparatus and the method used is further illustrated with reference to the following examples.

EXAMPLE 1

A prototype resonator-sensing unit was set up as illustrated in FIGS. 4–7. The main goal of these preliminary tests was to evaluate sensor functionality, operability, sensitivity and repeatability in the production environment. Variables examined were sensor plate separation distance, sensor operating mode (odd versus even), substrate material (nylon versus polyester), different constructions of the same material, different levels of adhesive (dip) pick-up, sensor plate design variations, and different line speeds.

The data provided in this example, except where indicated, is provided using a frequency scale range of 1.4 megahertz. Lower frequency values translate to higher moisture (dip) on the fabric for the data provided. Frequency values in the various sets of data should not be compared because of experimental differences, which may exist between the different experiments. The data only shows relative correlation.

The sensor plate optimized for our application was 300 mm by 60 mm in size, which produced a frequency that was compatible with our electronic equipment requirements. The separation between the two plates was set at 120 mm. This produced the best sensitivity and accuracy for the current application. However, the separation can range from 10 mm to 200 mm and still produce accurate measurements.

The sensor is more accurate in the vertical orientation. Moreover, the orientation of the resonator plates from zero degrees (vertical) to ninety degrees (horizontal) will change coverage area and accuracy.

Two identical sized resonator (sensor) plates were placed on either side of the fabric as it exited the vacuum heads. A high frequency signal of 350 megahertz from the network analyzer excited a field between the two plates. Moisture in the fabric changes the reflective frequency between the plates and the analyzer measures the shift in the frequency disturbance. The resonator plates are attached to a shielding structure (grounding plates) to eliminate influences from the ambient surroundings, such as movement of the machine operator in the area. The trial unit used two large sized plates mounted on a tubular structure so that it could be slid toward and away from the fabric.

When optimal distances are established, and optimal plate sizes are established, it is contemplated that, in production, an array of sensor plates can be used which will be disposed across the full width of the fabric. In these trials, the pair of plates was centered on the fabric.

The unit was installed after the first dewebber head.

The unit was checked for drift caused by ambient temperature and humidity changes. This required monitoring the even and odd frequency modes, and subtracting the difference. If the difference remains constant in ambient conditions, the sensor is functioning properly. Since, in the test, the difference appeared to be constant, only the even mode was monitored in most of the trials. It was noted in the trials, however, that when personnel came close to the resonator unit, the moisture measurement was affected. Therefore, the geometry effectiveness of the shielding (ground) plates must still be evaluated.

The sensor plate design was evaluated. Thicker, rectangular shaped sensor plates acted similar to thinner sensor plates. It was decided to use the thicker, more robust plates.

An hourglass shaped sensor plate was tried instead of the standard rectangular plate, and the quality factor (Q factor or sharpness of the signal) was improved significantly. It was found, however, that there appeared to be more noise with this shaped plate, and it was decided that the plate shape needed to be optimized.

The sensor plates worked well with a 10-centimeter separation between the plates. A 20-centimeter separation was tried, and although a signal was achieved, there was less sensitivity at this distance. The distance between the sensing plates must be held rigid during sensing since a 2-millimeter shift between the sensors can cause a 100 kilohertz frequency shift in the resonance point.

Although there appeared to be no dip contamination of the plates during this test, it is contemplated that the sensor plates can be coated for easy cleaning, such as with a plastic coating.

Samples of nylon fabric and polyester fabric were processed during the evaluation. It was noticed that nylon tends to have a moisture content in the fabric of between 3% and 6%, and the moisture is normally higher on the face and side edges of the roll rather than the interior section of the roll. Also, it was noted that the first wraps in the roll have significantly more moisture than the remaining portion of the roll. This indicates that there needs to be adjustment for moisture in the fabric in different portions of the fabric roll.

It was noted that polyester absorbs very little moisture from the atmosphere, and it was further noted that polyester tends to absorb less dip than nylon. Initial resonator results indicated a higher dip pick-up for the polyester than nylon. Various theories were proposed to account for this variation, one of which is that the polyester has a different dielectric constant than nylon, and it is the fabric itself which causes a frequency level shift, which indicates a need for accurate calibration for each particular material that is used in the fabric processing unit.

During a test it was shown that the unit was effective for sensing the following:
(1) Changes in the amount of dip pick-up when the fabric was slowed down but the deweber fan was held at a constant speed.
(2) Changes in the amount of dip pick-up when the let-off accumulator was raised or lowered. In this instance, it is believed that tension oscillations downstream due to the fabric feed rate change in the festoon makes the fabric more open, thus picking up more dip.
(3) The splice could be detected, since there is more dip on the splice, and it causes a sharp negative spike in the frequency graph.
(4) Streaking was sensed, indicating that the apparatus is sensitive to small changes in the amount of dip present on the fabric, and reinforcing the need to provide sensors across the fill width of the fabric, since a streak may not be detected if the sensor plates are not in the area of the streak.

(5) The drying of the fabric was observed during a stop of the dip unit. The frequency observed by the sensors changed exponentially as the material dried.

(6) Different yarn suppliers use different finishing oils, and, therefore, the fabrics may have higher or lower moisture absorption rates. Differences in the amount of pick-up on fabrics that have the same specifications, but are made with yarn provided by different suppliers was detected by the resonator. It showed a different dip pick-up for the same vacuum setting.

(7) Changing the deweber fan speed for the same code of fabric showed a difference in the detector frequency signal level. This may give guidance to a relationship between frequency change and the amount of dip picked up.

Figure 15:
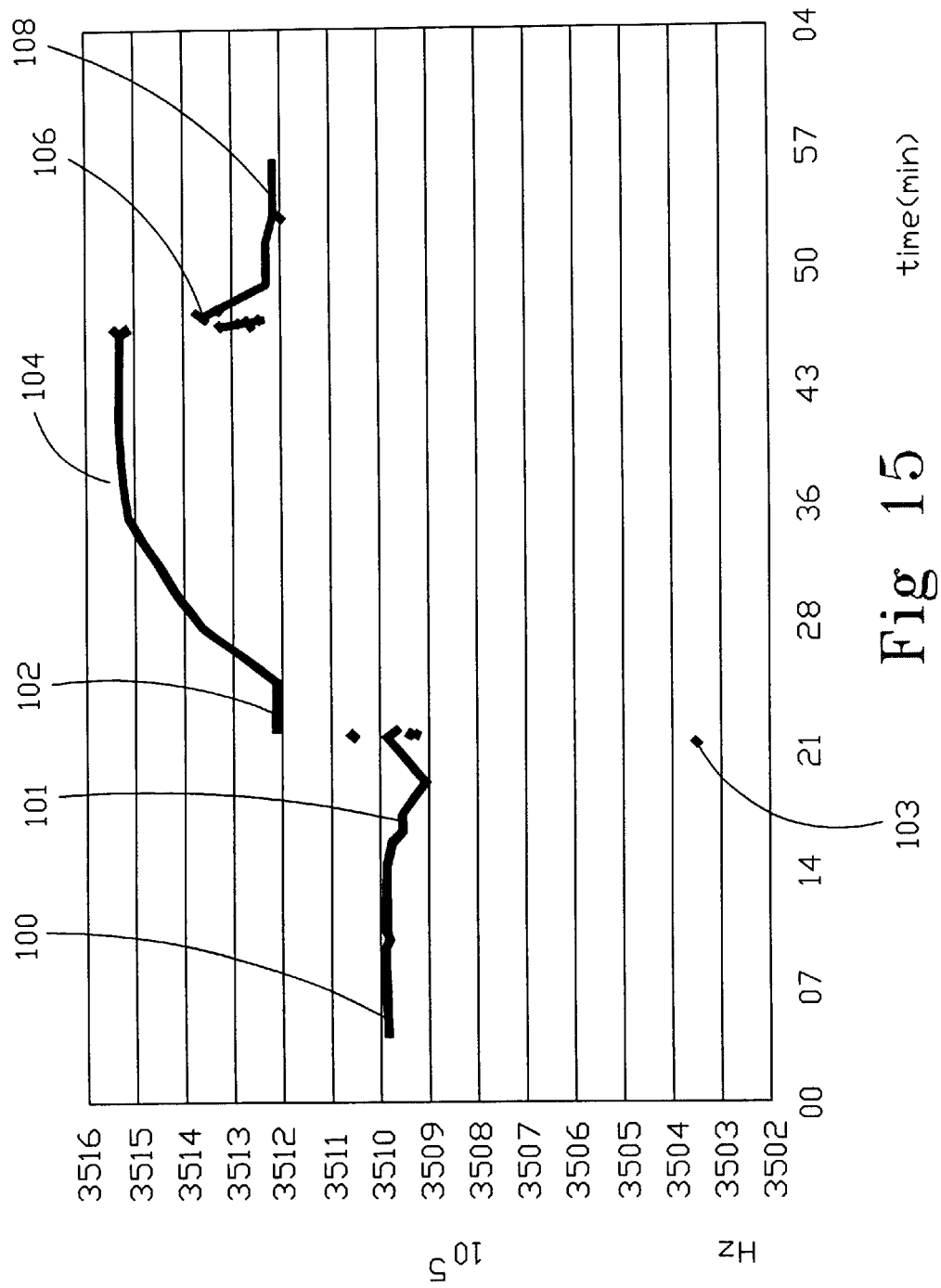
FIG. 15 illustrates sensor readings obtained using an experimental prototype of the apparatus of the invention.

FIG. 15 illustrates the sensitivity of the apparatus to a fabric change. The signal 100 is obtained from the tail end of the fabric roll as the splice between the old roll and the new roll approaches. Portion 101 of the signal indicates where the let-off festoon started to fill with fabric, and point 103 represents the splice between the two fabrics passing between the resonator plates. The initial signal 102 of the new roll of fabric indicates some differences between the old roll of fabric and the new roll of fabric. The line was stopped as the changeover was made, and the raised end portion of the signal 104 indicates the change in frequency as the fabric continued to dry between the resonator plates. Portion 106 of the signal indicates when the unit restarted, and portion 108 indicates where the signal returned to the previous level. Unexpectedly, these signals indicate great sensitivity for the sensor system used.

Figure 16:
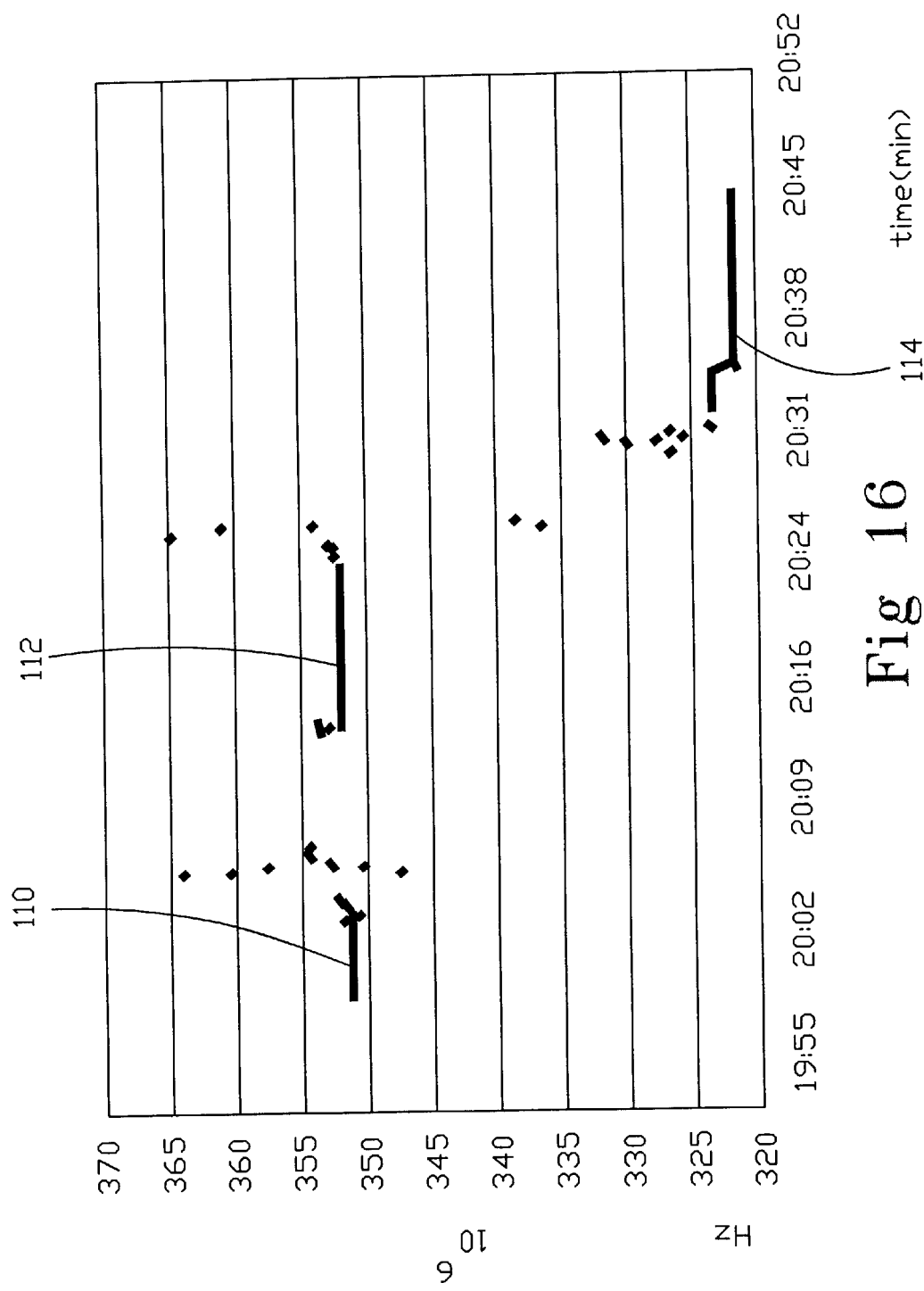
FIG. 16 illustrates additional data showing the functionality of the apparatus of the invention.

With reference to FIG. 16, signals obtained using different plates are observed. Signal 110 indicates the results obtained using a thick rectangular plate, and signal 112 indicates the results obtained from a thin rectangular plate. Signal 114 indicates the signal obtained from an hourglass shaped plate. These results indicate a different frequency for the sensor plate having an hourglass shape.

Figure 17:
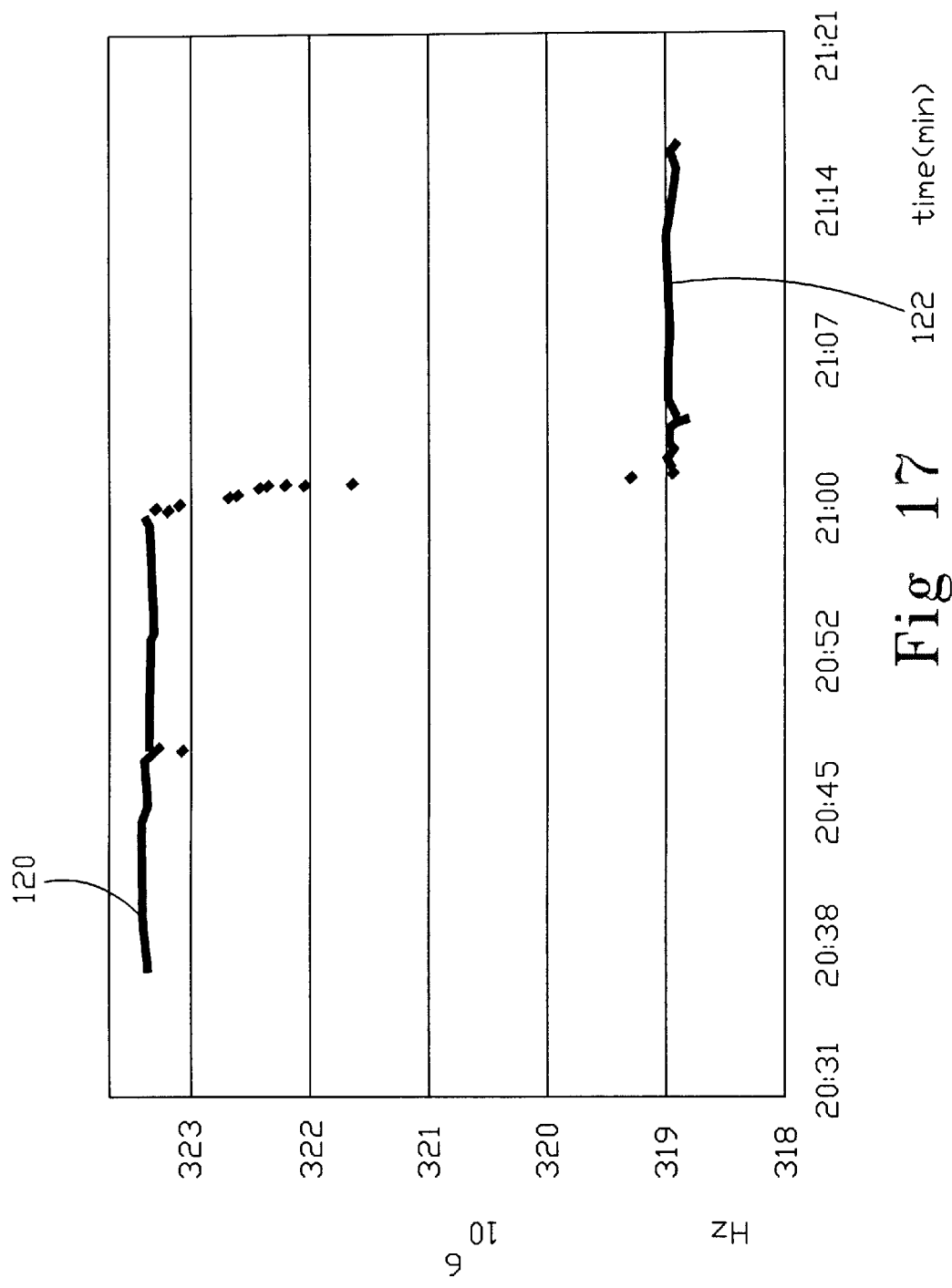
FIG. 17 illustrates additional data showing the functionality of the apparatus of the invention.

FIG. 17 illustrates the difference between the signals obtained when the sensor plates are 10 centimeters apart (i.e., 5 centimeters on each side of the fabric) and the signal obtained when the plates are 20 centimeters apart. Signal 120 illustrates the sensitivity for the 10-centimeter spacing, and signal 122 indicates the sensitivity at the 20-centimeter spacing. Given the sensitivity change noted, it was decided to maintain the 10-centimeter spacing for the trials.

Figure 18:
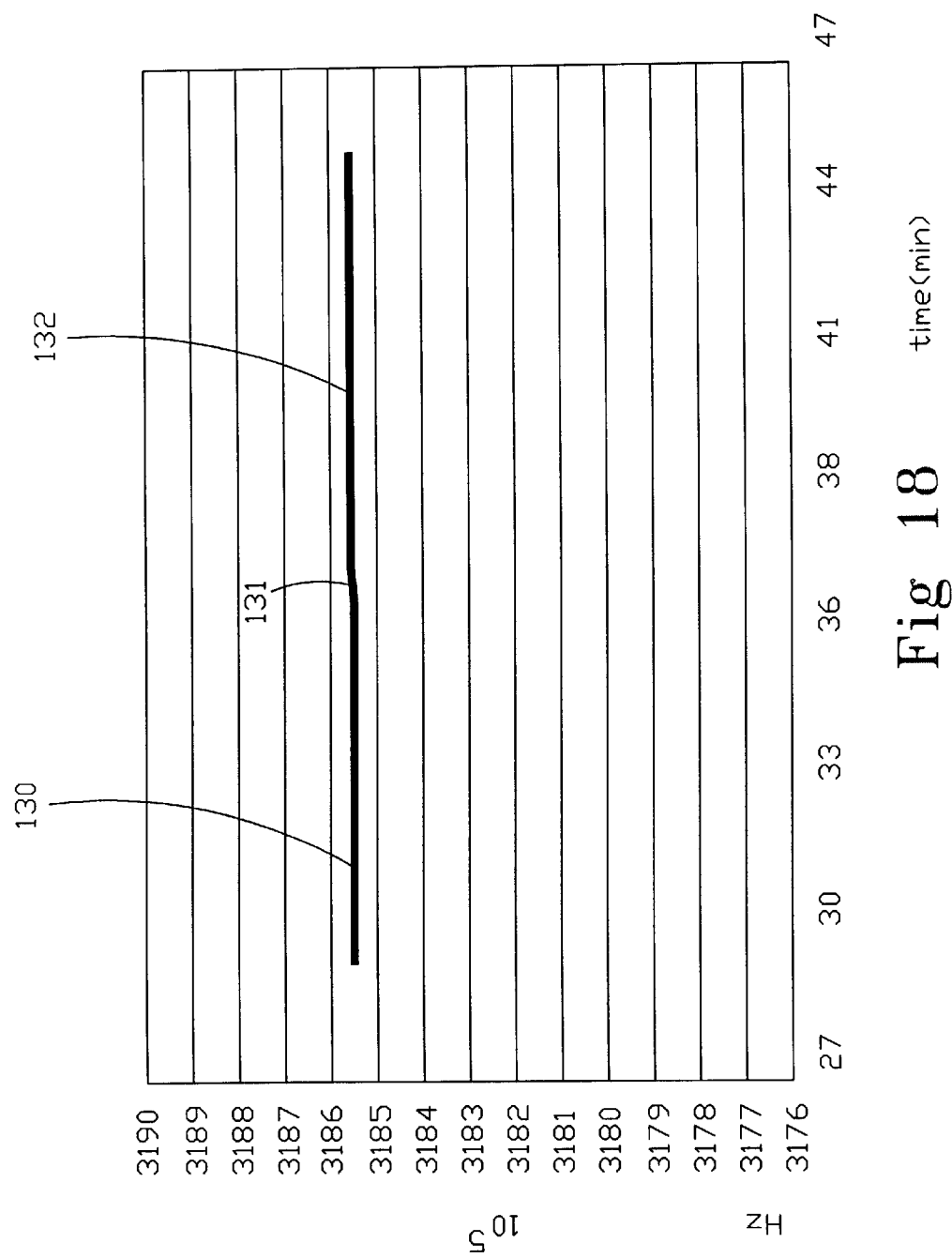
FIG. 18 illustrates additional data showing the functionality of the apparatus of the invention.

FIG. 18 illustrates the signal obtained using butterfly shaped sensors (hourglass shaped) having a 20-centimeter spacing. The shift 131 in the signal indicates a change in two different kinds of yarn in the fabric roll. Signal 130 represents a steady state for the first type of yarn, and signal 132 shows a steady state for the second yarn.

Figure 19:
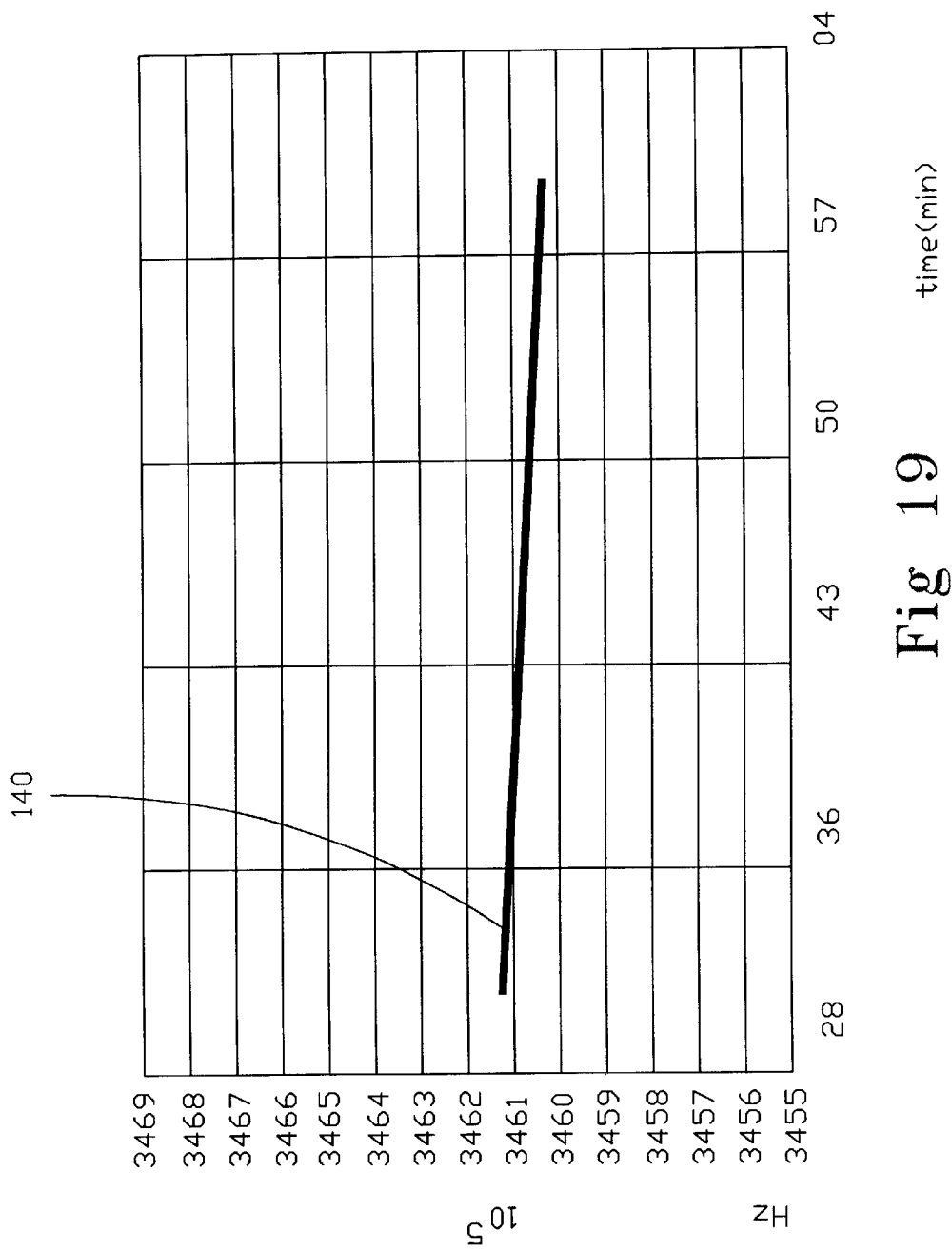
FIG. 19 illustrates additional data showing the functionality of the apparatus of the invention.

FIG. 19 illustrates a streaking incident on the fabric. The slope of the signal 140 indicates increasing amounts of dip picked up on the fabric. The signal again indicates the great sensitivity obtained using the apparatus of the invention.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A method for applying a liquid polymer to a substrate comprising the steps in the following order:

(a) applying a liquid polymer to a substrate with a liquid polymer depositing means;

(b) passing the coated substrate through a resonant cavity sensor;

(c) sensing the amount of liquid polymer applied to the substrate with a resonant cavity sensor;

(d) passing the coated substrate in a vacuum means;

(e) removing any excess polymer from said substrate with the vacuum means, and (g) using information from the resonant cavity sensor to control the amount of liquid polymer remaining on the substrate after the substrate passes through the vacuum means.

2. The method of claim 1 wherein a dipping operation is used to apply the liquid polymer in step (a).

3. The method of claim 1 wherein substrate is a fabric and the liquid polymer is an adhesive containing solids and liquids and information from the sensor is combined with information regarding i) the specification of the fabric, ii) the speed at which the fabric passes through the liquid polymer dispensing means, the sensor, or the vacuum means, iii) the adhesive formula, and iv) the solids content of the adhesive, in order to control the polymer application in addition to controlling the vacuum means.

4. The method of claim 1 comprising the further step of using information from the sensor in step (c) to control the vacuum to remove excess polymer in step (e).

5. The method of claim 1 comprising the further steps of:

(g) prior to step (a) establishing a first resonant frequency base line for a specific substrate;

(h) prior to step (a) establishing a second resonant frequency base line for said substrate coated with a desired amount of polymer; and controlling the vacuum in step (e) in said vacuum means using said resonant frequency base lines such that when the content of polymer on said substrate is too high the vacuum is increased and when the content of the polymer is too low the vacuum is decreased.

6. The method of claim 1 comprising the further steps of:

(g) prior to step (a), establishing a first resonant frequency base line for a specific substrate;

(h) prior to step (a), establishing a second resonant frequency base line for said substrate coated with a desired amount of polymer; and controlling the rate of speed at which said substrate passes through the liquid polymer depositing means and the vacuum means using said resonant frequency base lines such that when the polymer content on the substrate is too high the rate increases and when the polymer content is too low the rate decreases.

\* \* \* \* \*